United States Patent [19]
Gray et al.

[11] Patent Number: 6,149,576
[45] Date of Patent: Nov. 21, 2000

[54] TARGETED HYSTERESIS HYPERTHERMIA AS A METHOD FOR TREATING TISSUE

[75] Inventors: Bruce Nathaniel Gray, Claremont; Stephen Keith Jones, Scarborough, both of Australia

[73] Assignee: Paragon Medical Limited, Western Australia, Australia

[21] Appl. No.: 09/182,580

[22] Filed: Oct. 29, 1998

[30] Foreign Application Priority Data

Oct. 29, 1997 [AU] Australia ................................. PP 0081

[51] Int. Cl.$^7$ .................................................. A61B 17/52
[52] U.S. Cl. .................................... 600/9; 600/10; 600/12
[58] Field of Search .................................... 600/9, 10, 12

[56] References Cited

U.S. PATENT DOCUMENTS

| | | |
|---|---|---|
| 4,106,488 | 8/1978 | Gordon . |
| 4,303,636 | 12/1981 | Gordon . |
| 4,323,056 | 4/1982 | Borrelli et al. . |
| 4,545,368 | 10/1985 | Rand et al. . |
| 4,662,359 | 5/1987 | Gordon . |
| 4,983,159 | 1/1991 | Rand . |
| 5,411,730 | 5/1995 | Kirpotin et al. . |

OTHER PUBLICATIONS

Gilchrist et al., Selective Inductive Heating of Lymph Nodes, Annals of Surgery, Oct. 1957, vol. 146, No. 4, pp. 596–606.

Rand et al., Selective Radiofrequency Heating of Ferrosilicone Occluded Tissue: A Preliminary Report, Bull. Los Angeles Neurol. Soc. 41(4) pp. 154–159, 1976.

Mosso et al., Ferromagnetic Silicone Vascular Occlusion: A Technic for Selective Infarction of Tumors and Organs, Ann. Of Surgery, Nov. 1972, pp 663–668.

Rand et al., Ferromagnetic Silicone Vascular Occlusion in a Superconducting Magnetic Field Preliminary Report, Bull. Los Angeles Neurol. Soc., 1972, 37: pp 67–74.

Rand et al., Thermomagnetic Surgery for Cancer, Journal of Surgical Research vol. 33, No. 3, Sep. 1982, pp. 177–183.

Rand et al., Thermomagnetic Surgery for Cancer, Applied Biochemistry and Biotechnology 6, pp. 265–272 1981.

Gordon et al., Intracellular Hyperthermia A Biophysical Approach to Cancer Treatment Via Intracellular Temperature and Biophysical Alterations, Medical Hypotheses 5: pp. 83–102, 1979.

Luderer et al, Glas–Ceramic–Mediated, Magnetic–Field–Induced Localized Hyperthermia: Response of a Murine Mammary Carcinoma, Radiation Research 94, pp. 190–198, 1983.

Borrelli et al., Hysteresis heating for the treatment of tumours, Phys. Med. Biol. 1984, vol. 29, No. 5, pp. 487–494.

Matsuki et al., High Quality Soft Heating Method Utilizing Temperature Dependence of Permeability and Core Loss of Low Curie Temperature Ferrite, IEEE Transactions on Magnetics, vol. MAG–21, No. 5, Sep. 1985.

(List continued on next page.)

*Primary Examiner*—Max Hindenburg
*Assistant Examiner*—Brian Szmal
*Attorney, Agent, or Firm*—Merchant & Gould P.C.

[57] ABSTRACT

The present invention provides an improved method for treatment of diseased tissue, which comprises the steps of:

(i) selecting at least a magnetic material which has a magnetic heating efficiency of at least about $4.5 \times 10^{-8}$ J.m./A.g, when rotational magnetic field conditions are equal to or less than about $5 \times 10^8$ A/m.s;

(ii) delivering the magnetic material to a patient's diseased tissue; and (iii) exposing the magnetic material to a rotational magnetic field with a frequency of greater than about 10 kHz and a field strength selected such that the product of field strength, frequency and the radius of the exposed region is less than about $7.5 \times 10^7$ A/s to generate hysteresis heat in the diseased tissue.

47 Claims, 8 Drawing Sheets

OTHER PUBLICATIONS

Matsuki et al., An Optimum Design of a Soft Heating System for Local Hyperthermia, IEEE Transaactions on Magnetics, vol. MAG–23, No. 5, Sep. 1987.

Matsuki et al., Performance of Soft Heating for Locat Hyperthermia Using Temperature Sensitive Amorphous Metal Flakes, IEEE Trancactions on Magnetics, vol. 25, No. 5, Sep. 1989.

Matsuski et al, Local Hyperthermia Based on Soft Heating Method Utilizing Temperature–Sensitive Ferrite Rod, IEEE Transactions on Magnetics, vol. 26, No. 5, Sep. 1990.

Yanada et al., Evaluation of Performance of Soft Heating Element for Local Hyperthermia, IEEE Translation Journal on Magnetics in Japan, vol. 6, No. 7, Jul. 1991.

Sato et al., Ferromagnetic Amorphous Metal Microcapsules for Intra–tissue Hyperthermia and Slow Release of Anti––Cancer Agents, Proc. 16th Annual Conference IEEE Embs.1. pp. 131–133, 1992.

Sato et al., Development of a New Heating Device and an Exciting Coil for Interstitial hyperthermia, Proc. 16th Ann. Conf. IEEE, pp. 234–235, 1992.

Sato et al., The Development of Anticancer Agent Releasing Microcapsule Made of Ferromagnetic Amorphous Flakes for Intratissue Hyperthermia, IEEE Transactions on Magnetics, vol. 29, No. 6, Nov. 1993, pp. 3325–3330.

Matsuki et al., Temperature–sensitive amorphous magnetic flakes for intratissue hyperthermia, Materials Science and Engineering, A181/A182, 1994, pp. 1366–1368.

Bartlett et al., On the use of ferromagnetic microparticles in microwave and radio frequency hyperthermia, Journal of the Institution of Electronic and Radio Engineers, vol. 58, No. 4, pp. 197–201, Jun. 1988.

Suzuki et al., Studies on Liposomal Ferromagnetic Particles and a Technique of High Frequency Inductive Heating, J. Jpn. Soc. Cancer Ther. 25(11): pp. 2649–2658, Nov. 1990.

Chan et al., Synthesis and evaluation of colloidal magnetic iron oxides for the site–specific radiofrequency–induced hyperthermia of cancer, Journal of Magnetism and Magnetic Materials 122, 1993, pp. 374–378.

Jordan et al., Inductive heating of ferrimagnetic particles and magnetic fluids: physical evaluation of their potential for hyperthermia, Int. J. Hypertermia, 1993, vol. 9, No. 1, pp. 51–68.

Jordan et al., Cellular uptake of magnetic fluid particles and their effects on human adenocarcinoma cells exposed to AC magnetic fields in vitro, Int. J. Hyperthermia, 1996, vol. 12, No. 6, pp. 705–722.

Mitsumori, Development of intra–arterial hyperthermia using a dextran–magnetite complex, Int. J. Hyperthermia, 1994, vol. 10, No. 6, pp. 785–793.

Mitsumori et al., Targeted Hyperthermia using Dextran Magnetite Complex: A New Treatment Modality for Liver Tumors, Hepato–Gastroenterology 43, 1996, pp. 1431–1437.

Shinkai et al., Antibody–conjugated magnetoliposomes for targeting cancer cells and their application in hyperthermia, Biotechnol. Appl. Biochem. 21, 1994, pp.125–137.

Suzuki et al., Preparation and characteristics of magnetite––labelled antibody with the use of poly(ethylene glycol) derivatives, Biotechnol. Appl. Biochem. 21, pp. 335–345, 1995.

Shinkai et al., Intracellular Hyperthermia for Cancer Using Magnetite Cationic Liposomes: In vitro Study, Jpn. J. Cancer Res. 87, pp. 1179–1183, Nov. 1996.

Jones et al., Evaluation of ferromagnetic materials for low––frequency hysteresis heating of tumours, Phys. Med. Biol. 1992, vol. 37, No. 1, pp. 293–299.

Jordan et al., Magnetic Fluid Hyperthermia (MGH), Scientific and Clinical Applications of Magnetic Carriers, Plenum Press, New York, 1997, pp. 569–595.

Bacri et al., Use of Magnetic Nanoparticles for Thermolysis of Cells in a Ferrofluid, Scientific and Clinical Applications of Magnetic Carriers, Plenum Press, New York, 1997, pp. 597–606.

Chan et al., Physical Chemistry and in vivo Tissue Heating Properties of Colloidal Magnetic Iron Oxides with Increased Power Absorption Rates, Scientific and Clinical Applications of Magnetic Carriers, Plenum Press, New York, 1997, pp. 607–618.

TARGETED HYSTERESIS HYPERTHERMIA AS A METHOD FOR TREATING TISSUE

The present invention relates to an improved means for treating a patient's tissue using targeted hysteresis therapy. In particular, it relates to a method of treating diseased tissue in a patient using site directed hysteresis heat release.

Diseases of the human body such as malignant tumours are generally treated by excision, chemotherapy, radiotherapy or a combination of these approaches. Each of these is subject to limitations which effects clinical utility. Excision may not be appropriate where the disease presents as a diffuse mass or is in a surgically inoperable locality. Chemotherapeutic agents are generally non-specific, thus resulting in the death of normal and diseased cells. As with chemotherapy, radiotherapy is also non-specific and results in the death of normal tissues exposed to ionising radiation. Furthermore, some diseases such as tumours may be relatively resistant to ionising radiation. This is a particular problem with the core of a tumour mass.

Hyperthermia has been proposed as a cancer treatment. There is a great deal of published evidence to confirm that hyperthermia is effective in treating diseases like cancerous growths. The therapeutic benefit of hyperthermia therapy is mediated through two principal mechanisms: (1) a directly tumouricidal effect on tissue by raising temperatures to greater than 42° C. resulting in irreversible damage to cancer cells; and (2) hyperthermia is known to sensitise cancer cells to the effects of radiation therapy and to certain chemotherapeutic drugs. The lack of any cumulative toxicity associated with hyperthermia therapy, in contrast to radiotherapy or chemotherapy, is further justification for seeking to develop improved systems for hyperthermia therapy.

Mammalian cells sustain hyperthermic damage in a time/temperature and cell-cycle dependant manner. This cellular response to heat is in turn modified by a variety of intra- and extra-cellular environmental factors. The intracellular factors that influence hyperthermic cell damage include intrinsic variation between different species, organs and even cell lines. The extra-cellular factors include the oxygen and nutritional status of cells, the pH of the extra-cellular milieu, the absolute temperature rise and the hyperthermic duration.

Although there is some evidence that neoplastic cells are more sensitive than their normal tissue counterparts to the effects of hyperthermia, this is not a universal finding and several recent studies have demonstrated that tissue susceptibility to hyperthermic damage is not strongly linked to a cell's neoplastic-normal status.

A number of studies have confirmed that hyperthermia and radiotherapy are synergistic. Even small fractions of a degree of temperature variation can significantly alter the prospects of cells surviving a radiation insult.

Factors affecting the synergistic action of hyperthermia and radiotherapy include the degree of duration of hyperthermia, the sequence of hyperthermia and radiotherapy, the fractionated and total dose of radiation, the pH of the extra-cellular milieu, the oxic state and nutrient status of cells and the histological type and malignant status of the cells.

Cells in the central avascular compartment of tumours are invariably acidotic hypoxic and in a state of nutritional deprivation. All these factors appear to potentiate independently the effect of hyperthermia. By the same token, severely hypoxic cells are approximately three times more resistant to ionising radiation than oxic cells. Of major importance is the fact that although these hypoxic cells might survive the effects of radiation, hyperthermia can partly overcome this radioresistance and can potentiate radiotherapeutic killing of acidotic and hypoxic cells.

There are many problems associated with the currently available methods for inducing clinical hyperthermia in patients. Normal body tissues and organs are heat sensitive and at temperatures of greater than 42° C. many tissues will undergo irreversible damage. The current available methods of delivering clinical hyperthermia are non-specific and will heat normal tissues as well as tumour cells. Almost all heating techniques create heat generation over a broad target area with little specificity for diseased tissue, although focussing devices for both ultrasound and electromagnetic heat generation are now being developed to improve the concentration of heat generation in more defined target areas.

Several techniques are currently available for inducing clinical hyperthermia either regionally, in selected local regions of specific organs or over the whole body. Some of these techniques are discussed below.

Whole body hyperthermia may be induced by endogenous or exogenous heat sources, but is generally not tolerated above 42° C. without anaesthesia. Regional hyperthermic techniques include organ perfusion, various forms of electromagnetic radiation, or ultrasound.

Plain wave electromagnetic or ultrasound heating is limited by poor tissue penetration and a rapid decline of energy with increasing depth.

Ultrasound at frequencies of from 0.3 to 3 MHz is limited by the perturbations induced by tissue interfaces such as air, bone etc. Improved focussing devices are however, being developed that may make this a more acceptable form of heating for deep tissues.

Microwave heating at frequencies between 434 and 2450 MHz has been used, although there is generally poor tissue penetration. Phase array devices are able to focus microwave energy in deep tissues, but variation in the heating effect remains a problem.

Radiofrequency waves at frequencies up to 434 MHz have been used with some success. These heating techniques include both dielectric and inductive modalities and can result in relatively even tissue heating. However, focussing for deep organ heating using inductive current remains a problem.

There are two basic requirements for such therapies to be effective. First, there is a need to localise the treatment to the target site. Second, there is a need to maximise heating within the diseased tissue while maintaining hyperthermia therapy within safe operating limits for the patient.

While considerable success has been observed in treating superficial tumours using hyperthermia therapy, there remains a need for a method of selectively targeting and treating diseased tissue in a patient. Major limitations due to insufficient penetration depth and poor focussing capabilities of externally applied microwave or ultrasound beams have grossly restricted a physicians ability to deliver an adequate heat load to deep seeded diseased without any unacceptable level of coincident damage to surrounding healthy tissue. The present invention seeks to ameliorate at least the problems associated with penetration depth and inadequate localisation of heat when using hyperthermia therapy.

Throughout this specification, unless the context requires otherwise, the word "comprise", or variations such as "comprises" or "comprising " will be understood to imply the inclusion of a stated integer or group of integers, but not the exclusion of any other integer or group of integers including method steps.

SUMMARY OF THE INVENTION

Thus the present invention relates to a method for heating a substance, comprising the steps of:

(i) selecting at least a magnetic material which has a magnetic heating efficiency of at least about $4.5 \times 10^{-8}$ J.m./A.g, when rotational magnetic field conditions are equal to or less than about $5 \times 10^8$ A/m.s;

(ii) introducing the magnetic material into the substance; and (iii) exposing the magnetic material to a rotational magnetic field with a frequency of greater than about 10 kHz and a field strength selected such that the product of field strength, frequency and the radius of the exposed region is less than about $7.5 \times 10^7$ A/s to generate hysteresis heat in the substance.

In one embodiment of the invention the substance is of a non-biological nature and includes such materials as rubber, microcapsules and plastics.

In an alternative embodiment of the invention there is provided a method for treating biological tissue, comprising the steps of:

(i) selecting at least a magnetic material which has a magnetic heating efficiency of at least about $4.5 \times 10^{-8}$ J.m./A.g, when rotational magnetic field conditions are equal to or less than about $5 \times 10^8$ A/m.s;

(ii) introducing the magnetic material into the biological tissue; and (iii) exposing the magnetic material to a rotational magnetic field with a frequency of greater than about 10 kHz and a field strength selected such that the product of field strength, frequency and the radius of the exposed region is less than about $7.5 \times 10^7$ A/s to generate hysteresis heat in the diseased tissue.

The present invention may be used to treat any tissue that is sensitive to thermotherapy, chemotherapy or radiotherapy or a combination of thermotherapy and chemotherapy or radiotherapy. Preferably, the invention is employed to treat cancerous growths or tissue which contains one or more tumours.

Although the following discusses use of the method for cancer/tumour treatment, it should be appreciated that applications of the method extend beyond merely treating cancer/tumours. Any disease state that can be cured by killing diseased cells can be treated by the method. In this context the method is not limited to killing cells only by the generation of hysteresis heat.

The above method may be performed either in vitro or in vivo, depending upon whether the diseased tissue to be treated can be removed from the patient. Preferably the method is performed in vivo. Reference to the treatment of a patient should not be understood to be limited to treating humans. Such a reference includes the treatment of any animal.

Preferably, step (iii) of the method is carried out for sufficient time to generate enough heat from the administered magnetic material to raise tumor temperature above about 42° C. It will be appreciated that the amount of time for treating a tumor will largely depend on the size, position and physical structure of the tumor. Most preferably steps (i) to (iii) are repeated until the diseased tissue has been destroyed or treated sufficiently to ameliorate the disease.

Preferably the magnetic materials used in the invention are bound within a matrix to form microcapsules. While the microcapsles may be of varying sizes they are preferably of a size large enough to pass through a patient's vasculature network and become dispersed and embolised within diseased tissue. Microcapsules used in the method may, for example, be prepared to release a particular therapeutic or toxic chemical only when hysteresis heat reaches a certain predetermined temperature.

The magnetic material employed in the method must have a magnetic heating efficiency (MHE) of greater than about $4.5 \times 10^{-8}$ J.m./A.g, when magnetic field conditions are equal to or less than about $5 \times 10^8$ A/m.s. Preferably, a magnetic material is selected which has a MHE of greater than about $7 \times 10^{-8}$ J.m./A.g, when magnetic field conditions are equal to or less than about $5 \times 10^8$ A/m.s. Most preferably, a magnetic material is selected which has a MHE of greater than about $1 \times 10^{-7}$ J.m./A.g, when magnetic field conditions are equal to or less than about $5 \times 10^8$ A/m.s.

Advantages gained by using a magnetic material with a large MHE include:

1) improved therapeutic effectiveness by virtue of the fact that higher tumour temperatures can be reached more quickly (the effectiveness of hyperthermia therapy improves markedly as temperature is increased beyond 42° C.);

2) reduced toxic side effects because:
   i/. less microcapsules need to be used to achieve therapeutic heating in tumours (advantageous if the microcapsules have any intrinsic toxicity),
   ii/. a lower magnetic field strength, H, can be used,
   iii/. more rapid heating of the tumour may be achieved which implicates less of the healthy tumour tissue immediately surrounding the tumour (the longer time required to heat the tumour the more the immediately surrounding tissue will be heated by thermal conduction);

3) increased likelihood of successful treatment especially for tumours that would otherwise be expected to only receive a marginal benefit;

4) the techniques have a wider applicability for the treatment of different types of cancer;

5) using reduced field strengths eases engineering difficulties associated with machine design;

6) using reduced field strengths means reduced electrical power consumption and cooling requirements while running the machine.

The selection of magnetic material suitable for use in the present invention is preferably dictated by the MHE of the material. A material's MHE may be calculated using the following formula:

$$MHE = \frac{P_{hyst}}{f \cdot H} \quad (J \cdot m / A \cdot g) \tag{1}$$

where $P_{hyst}$ is the heating power generated by magnetic hysteresis loss effects (units W/g), H is the amplitude of the applied magnetic field (units A/m) and f is the frequency of the applied magnetic field. The major limitations to the generation of heat by magnetic hysteresis for the purposes of treating diseased tissue, arise from the effect a time varying magnetic field has on living tissue. In general, these effects increase as the product of f and H increases. Hence, it is essential that $P_{hyst}$ be maximised subject to minimising the product of f and H.

$P_{hyst}$ is measured by taking a known quantity of the magnetic powder, (for example 125 mg), and dispersing it in a volume of agar gel (3% agar dissolved in warm water for example 5 mls). A temperature probe is then inserted into the gel and the whole exposed to the rotating magnetic field of desired frequency and strength. From the resultant curve of temperature vs time it is possible to calculate $P_{hyst}$ at that particular frequency and field strength.

Any magnetic material which exhibits hysteresis and which has a MHE of greater than $4.5 \times 10^{-8}$ J.m./A.g, when rotational magnetic field conditions are equal to or less than about $5 \times 10^8$ A/m.s may be used in the present invention. Preferably, the magnetic materials are ferromagnetic or ferrimagnetic materials. Ferrimagnetic or ferromagnetic materials may include elements such as iron, nickel, cobalt, manganese, arsenic, antimony and bismuth, but are not limited to such elements. Classes of materials from which the magnetic material may be selected include $CrO_2$, gamma-ferric oxide (both cobalt treated and non-treated) and metallic iron, cobalt or nickel. Also ferrites of general form $MO.Fe_2O_3$ where M is a bivalent metal, eg. Mg, Mn, Fe, Co, Ni, Cu, Zn, Cd or Li, cobalt treated ferrites or magnetoplumbite type oxides (M type) with general form $MO.6Fe_2O_3$ where M is a large divalent ion such as Ba, Sr or Pb are all potentially useful magnetic materials in this application. Further, superparamagnetic, single domain particles may be used as the magnetic material. Most preferably, the ferromagnetic material is selected from the class of ferromagnetic materials known as gamma-ferric oxide, ($\gamma Fe_2O_3$).

Examples of suitable magnetic materials from which the magnetic materials might be selected include Co treated gamma-ferric oxide, some non-cobalt treated gamma-ferric oxides, cobalt treated ferrites and chromium dioxide.

The method of the invention provides a means to increase temperature in the area of diseased tissue to above 41° C. to decrease the viability of malignant cells. A decrease in the viability of malignant cells results in either cell death or increased cell sensitivity to the effects of ionising radiation or chemotherapeutic drugs.

During treatment, patients are placed into a machine that generates a rotating magnetic field of strength H and frequency f. A rotational magnetic field can be described mathematically as the superposition of two orthogonal linear alternating magnetic fields with a $\pi/2$ phase difference, i.e.

$$H = H_x \sin(2\pi ft) + H_y \sin(2\pi ft + \pi/2) \quad (3)$$

where $H_x$ and $H_y$ are linear alternating magnetic fields which combine to give H and f is their frequency of alternation. An advantage of the use of a rotational magnetic field compared to a linear alternating magnetic field of the same frequency and amplitude is that it leads to higher MHE of the magnetic materials. This in turn means that lower frequency and field strengths can be used in the method, if desired. The reasons for this improved MHE are as follows:

(i) At small fields the effect of a rotating field cannot be reliably deduced from separate measurements of the alternating hysteresis effects in the two orthogonal directions. In this case the hysteresis heat generated by the rotational field is at least equal to twice the heat that would be generated from a linear alternating field of the same amplitude. The orthogonal components cannot be assumed to be independent of each other and it is more instructive to consider the rotational hysteresis in terms of a torque with a phase lag between the applied magnetic field and the sample magnetisation (see equation (4) below).

(ii) The magnetic material delivered to the diseased tissue typically consists of a large number of randomly oriented acicular, sub-micron size ferromagnetic particles. If one considers each of the constituent ferromagnetic particles to be acting independently of each other then those particles that happen to be aligned to the direction of a linear alternating magnetic field will be less effected by shape demagnetisation than those aligned at an oblique angle to a linear alternating magnetic field whose value is less than the saturation field. Hence, in the case of a linear alternating magnetic field the aligned particles will be more effective heat generators than the oblique particles. On the other hand, exposing these particles to a rotating field (described by equation (3) above) results in more effective utilisation of the heating potential from all particles since the shape demagnetisation effect is eliminated.

In order that enough hysteresis heat energy is generated by the microcapsules to heat the diseased tissue, the rotational magnetic field used in the method must have a relatively high frequency. The higher the frequency the greater the rate of heating in the tissues that contain the magnetic material. However, the physiological response to high amplitude, high frequency magnetic fields limit the field amplitude and frequency that can be used in any clinical application. These limitations result from nerve muscle activation and eddy current heating which depends, inter alia, on the electrical conductivity of the tissue. Both of these are as a result of the electric fields induced in the tissue by the magnetic field.

For a linear alternating field the size of these potentially deleterious induced electric fields is proportional to the square of the product of H, f and the radius, r, of the exposed area normal to the direction of the field. The product of H, f and r largely defines the magnetic field conditions. Desirably, this product should not exceed a value of about $7.5 \times 10^7$ A/s, ie $H.f.r \leq 7.5 \times 10^7$ A/s. To illustrate this point consider the case of a linear alternating field applied perpendicularly to the body axis. In this case r is typically 0.15 m so the product of f and H should not exceed about $5 \times 10^8$ A/m.s.

These field conditions extend to the case of a rotational applied magnetic field by considering a rotational field to be the superposition of two orthogonal linear fields, as described by equation (3). In this case, each of the orthogonal linear field components of the rotational field should separately conform to the product of H, f and r not exceeding a value of about $7.5 \times 10^7$ A/s.

The magnetic material used in the invention may be delivered to the diseased tissue in a patient by any means known in the art. Suitable routes of administration might include: intratumoral, peritumoral and intravascular administrations (eg intra-arterial, intraperitoneal, subcutaneous or intrathecal injections). Preferably, the magnetic materials are delivered to the diseased tissue via the arterial or venous blood supply.

Preferably, the magnetic material is mixed in a liquid emulsion or is formed into microcapsules that may then be mixed with a suitable biocompatible medium for delivery into a patient. Most preferably the magnetic material is bound in a matrix material to form a microcapsule. Most magnetic particles themselves are, typically, too small and too dense to enable optimum delivery to the site of diseased tissue. Therefore, they are desirably encapsulated in microcapsules. Important properties of microcapsules are their density and their diameter. The density effects the efficiency of their carriage by the blood stream to the site of immobilisation in the diseased tissues vascular network while the size determines the proximity of the point of immobilisation to the diseased tissue.

Preferably, the magnetic material is constrained by a matrix material that does not adversely effect the hysteresis or eddy current heating properties of the magnetic particles. The non-toxic binder or matrix material may comprise any of the suitable non-toxic materials that are well known in the micro-encapsulation art. Suitable materials include, for example, proteins, polymeric resins such as styrene-divinylbenzene, biopol, albumin, chitosan etc.

In a preferred form of the invention, the microcapsules are adapted to bind or absorb or contain a cytotoxic material that is released upon heating of the microcapsule. For example the microcapsule may be composed of a porous, heat sensitive material which is non-toxic to and, preferably, inert to or compatible with animal tissue and which has embedded within it suitable magnetic material. The pores in the material are desirably filled with the cytotoxic compound. Upon hysteresis heating the micro-particles are capable of expanding, thereby permitting the release of the cytotoxic compound. Such particles should, however, be resistant to melting upon hysteresis heating. Thus, the use of such particles in the method of the present invention provides a single device with which combined chemotherapy and thermotherapy can be achieved to treat diseased tissue in a patient.

Another alternative delivery technique could be the injection or intravascular infusion of a suitable ferrocolloid that could consist, for example, of a suspension of magnetic microparticles in a liquid medium such as lipiodol. In this case the magnetic particles could range in size from subdomain nanometer size up to several microns.

A combination of different types of microcapsules may also be administered at the time of treatment to provide a multimodal treatment. Microcapsules may be either radioactive microcapsules or chemotherapeutic microcapsules together with the hyperthermic microcapsules described. Further, the targeted hyperthermia therapy may be used in conjunction with conventional radiotherapy and/or chemotherapy. The choice of treatments will depend upon the specific details of each case as it presents.

According to a further embodiment of the invention, an ionising radiation source may be applied to the locus of the diseased tissue in conjunction with a magnetic field, said tissue having microcapsules as herein described included therein. The radiation source may be microcapsules that contain a radioactive compound such as Yttrium-90 or delivered from an external radiation source.

DETAILED DESCRIPTION OF THE INVENTION

The following non-limiting Figures, Description and Examples seek to illustrate the present invention. In the drawings.

Figure 5:
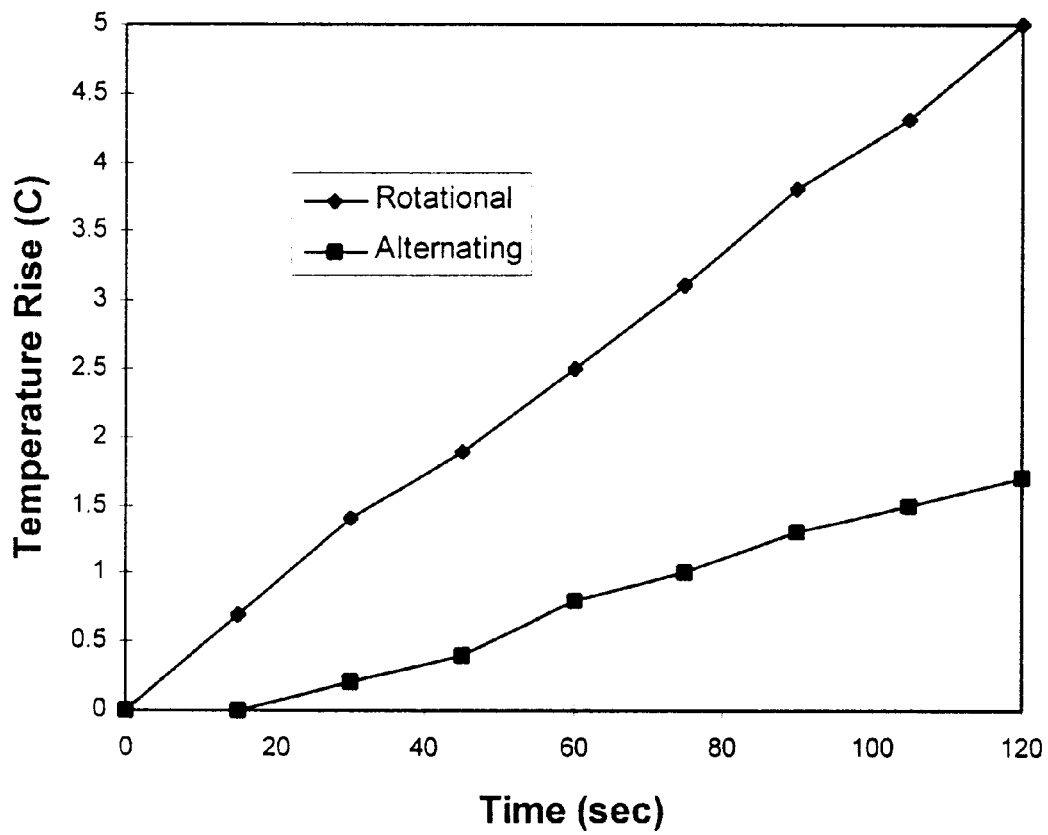

FIG. 5 provides a comparison of heating; rotational magnetic field vs linear alternating magnetic field for S11 magnetic material.

Figure 6:
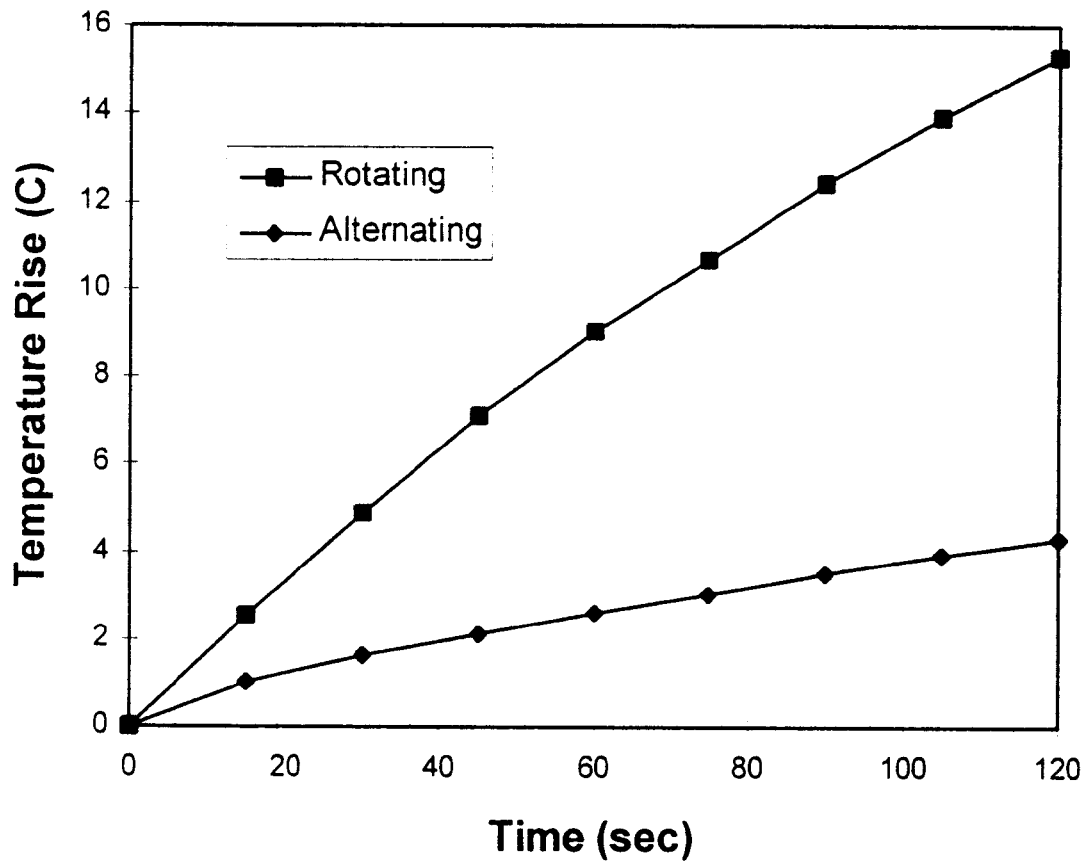

FIG. 6 provides a comparison of heating; rotational magnetic field vs linear alternating magnetic field for PCF35HT4 magnetic material.

Figure 7:
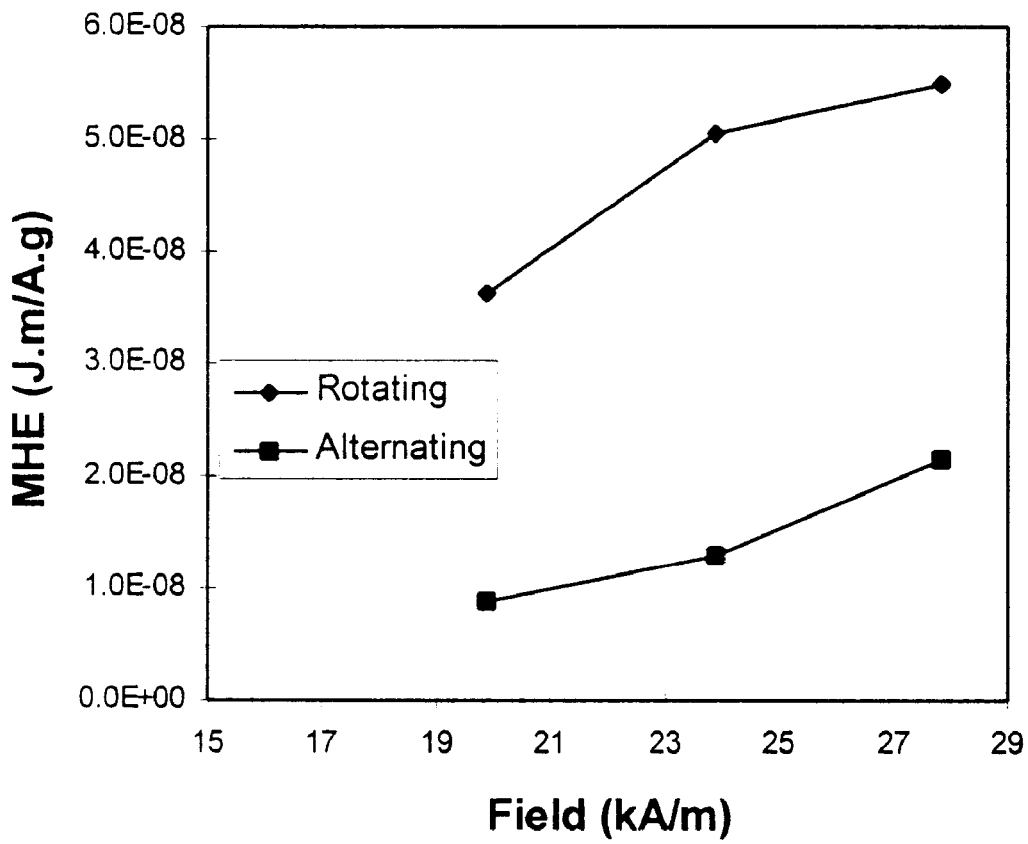

FIG. 7 provides a comparison of Magnetic Heating Efficiency (MHE) as a function of applied field for rotational magnetic field and linear alternating magnetic field for PCF35HT4 magnetic material.

Figure 8:
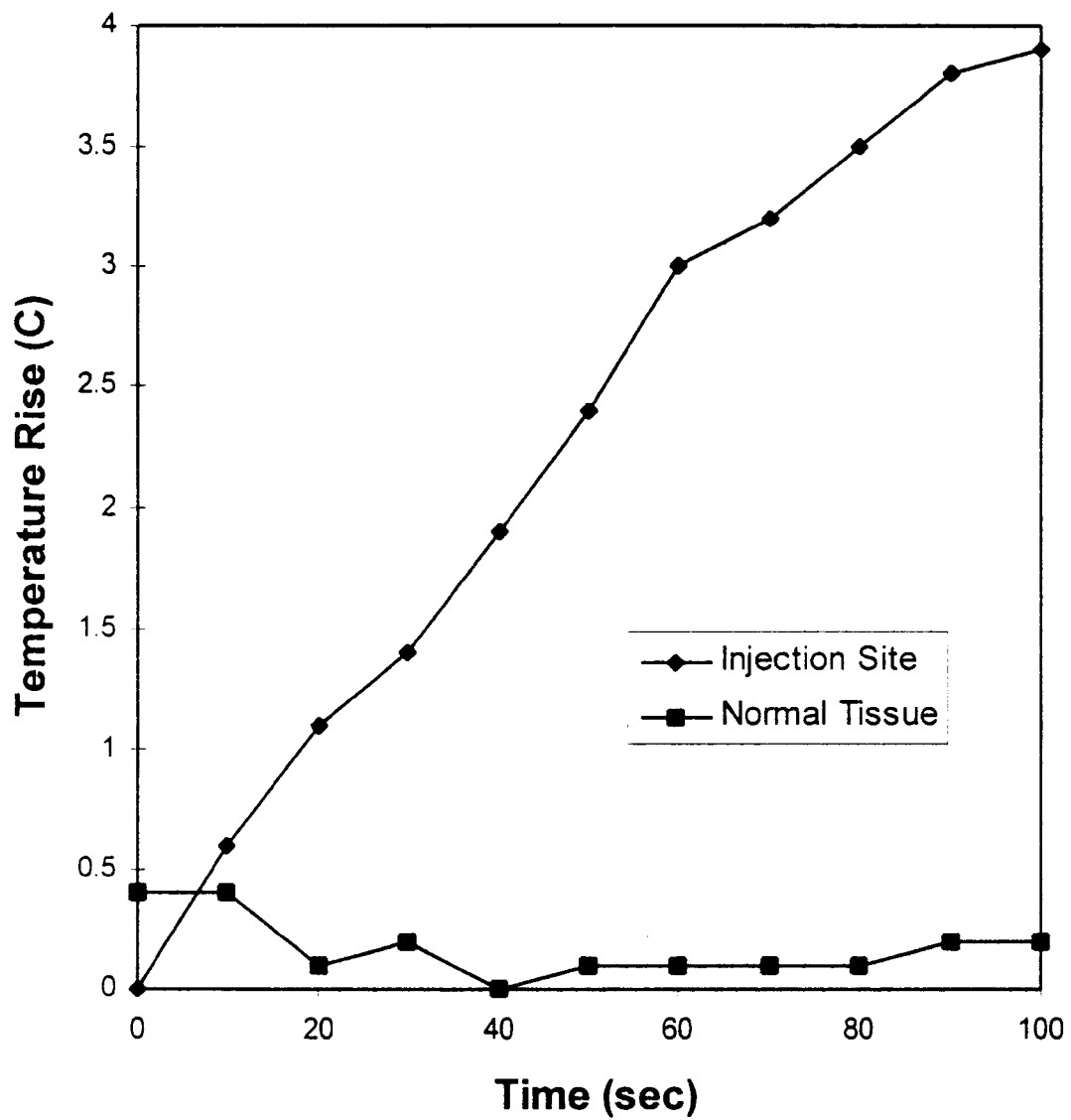

FIG. 8 shows site-specific heating of tissue using rotational magnetic field with injected magnetic particles.

Generation of heat in a range of greater than about 41° C. to 42° C. or higher (hyperthermia) causes irreversible damage to diseased cells. Thus, diseased tissue may be treated by elevating the diseased tissue's temperature (thermotherapy) as a result of hysteresis heat loss from suitable magnetic materials. Preferably, the heat generated by hysteresis heating is in the range of 42° C. to about 60° C.

When a magnetic substance is subjected to a rotational magnetic field with a strength that varies cyclically, some heat is generated due to magnetic hysteresis loss. The amount of heat generated per cycle depends on the hysteresis loss which varies for each different ferromagnetic material and for different magnetic field conditions. Magnetic particles embedded around a tumour site and placed within a rotating magnetic field will heat up to a temperature dependent on the magnetic properties of the material, the strength of the magnetic field, the frequency of rotation and the cooling capacity of the blood flow in the tumour site.

Figure 1:
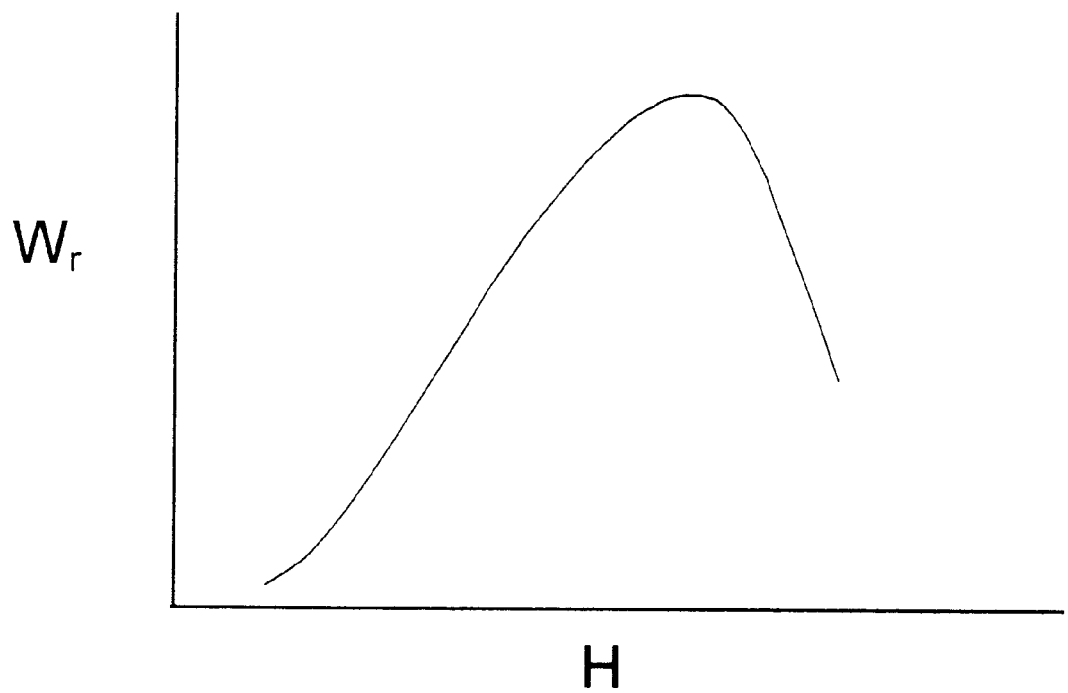
FIG. 1 illustrates a typical form of rotational work per cycle, W, as a function of applied field, H.

Energy in the form of heat is produced as a result of magnetic hysteresis loss in a ferromagnetic sample whenever it is subjected to a rotational magnetic field. The heating power generated by hysteresis effects is given by $$P_{hyst} = \frac{2\pi \times 10^{-3}}{\rho T^2} \int_0^T (H \times M) dt \quad W/g \qquad (4)$$

where $\rho$ is the density of the ferromagnetic material, T is the period of rotation (=1/f) of the applied magnetic field, H is the applied magnetic field and M is the magnetisation of the ferromagnetic sample. The quantity $$2\pi f \int_0^T (H \times M) dt$$

is equal to W, the amount of hysteresis energy generated by the magnetic material during each cycle of the applied magnetic field. A typical curve of W as a function of H is shown in FIG. 1. There is a clear peak in W as H is increased from zero.

To determine the minimum amount of heat that must be generated from the magnetic microcapsules for them to be an effective therapeutic agent, $P_{tumour}$ (W/cm$^3$) needs to be ascertained. $P_{tumour}$ is given by:

$$P_{tumour} = f \cdot W_c \cdot \rho \cdot v \cdot n (W/cm^3) \qquad (5)$$

where
f the frequency of the applied magnetic field in Hz,
$W_c$ the amount of heat energy generated by hysteresis effects in the injected magnetic microcapsules each cycle of the rotational magnetic field, units of J/g,
$\rho$ the density of the injected microcapsules in units of g/cm$^3$,
v the volume of each microcapsules in units of cm$^3$,
n the number of microcapsules per cm$^3$ of tumour tissue.

$P_{tumour}$ in essence represents the rate of tumour tissue heating. When related to the present invention Ptumour should be large enough that it causes the temperature of the tumour tissue to increase from body temperature to a temperature that is lethal to the diseased cells over a reasonable period of time.

Moreover, $P_{tumour}$ should be great enough to overcome tissue-cooling influences such as blood flow and tissue thermal conductivity. Preferably, $P_{tumour}$ is greater than 60 mW/cm$^3$. Most preferably it is greater than 80 mW/cm$^3$ and desirably it is greater than 100 mW/cm$^3$.

To obtain $P_{tumour}$ values in the preferred range, suitable values need to be selected for the variables f, $W_c$, ρ, v and n.

Available experimental data concerning human responses to oscillating magnetic fields is limited. Such data has lead to the identification of an optimal operational frequency range between about 10 kHz and 100 MHz. For frequencies less than this there is the danger of involuntary neuromuscular activation and for higher frequencies limitations begin to arise due to reduced penetration of the electromagnetic energy into the tissue. Therefore, the frequency should be maintained within the range 10 kHz to 100 MHz. Preferably the frequency is maintained with the range 10 kHz to 500 kHz. Most preferably the frequency is maintained with the range 10 kHz to 100 kHz and desirably it would not exceed 50 kHz. For example, the frequency is 20 kHz.

W (J/g) is an intrinsic property of the magnetic material incorporated into the microcapsules. A typical curve showing how W varies as a function of H is shown in FIG. 1. There are, however, limits to the amount that H can be increased when applying the method to patients. Such limits are also dependent on the frequency used and the area of tissue exposed to the magnetic field. The magnetic material chosen for use in the microcapsules should have a MHE of at least about 4.5×10$^{-8}$ J.m./A.g, when rotational magnetic field conditions are maintained within safe operating limits for a patient. Preferably, a magnetic material is selected which has a MHE of greater than about 7×10$^{-8}$ J.m./A.g, when magnetic field conditions are equal to or less than about 5×10$^8$ A/m.s. Most preferably, a magnetic material is selected which has a MHE of greater than about 1×10$^{-7}$ J.m./A.g, when rotational magnetic field conditions are equal to or less than about 5×10$^8$ A/m.s.

The requirements for magnetic field strength and frequency will also depend on the properties of the microcapsules. These properties are accounted for by the parameters: ρ(g/cm$^3$), v(cm$^3$), and n per cm$^3$.

Microcapsules used in the method of the invention are preferably of a suitable size to pass through a patient's vasculature network and become dispersed and embolised within diseased tissue (with or without the assistance of vasoactive agents). Such capsules should then be capable of becoming entrapped in the precapillary and capillary network of organs, tumours or tissues without passing back into the general venous circulation. Preferably, the microcapsules are larger than about 10 microns in diameter so that they lodge in the tumour vascular supply, but they are smaller than about 500 micron so that they don't embolise in the blood vessels before reaching the tumour. Most preferably the microcapsules range in size between about 10 to 100 microns, with 30 to 40 microns being most desirable.

Smaller microcapsules less than 10 microns may also be used in the method if they become incorporated into tumour tissues by the process of endocytosis.

Moreover, the density of ferromagnetic material is preferably such, so as to allow the microcapsules to be carried by the bloodstream in a patient. The microcapsules preferably possess a density in the range 1 to 5 g/cm$^3$. Most preferably, the density should be between 1.8 to 3 g/cm$^3$. Desirably, the density is in the range 1.8 to 2.2 g/cm$^3$, for example 2 g/cm$^3$. Of course, any particle within these ranges may be employed in the present invention.

A number of different methods may be used to prepare the microcapsules using a diverse range of matrix materials and manufacturing techniques. In one preferred form of this invention, the microcapsules contain cobalt treated γFe$_2$O$_3$ particles as the ferromagnetic material, bound together using a Biopol matrix (a copolymer of (R)-3-hydroxybutyric acid and (R)-3-hydroxyvaleric acid). Using this matrix, magnetic microcapsules in a density range of 1.8–2.2 g/cm$^3$ and in a size range 20–50 microns can be obtained.

The magnetic microcapsules may be formulated in such a way as to regulate the temperature of the tumour temperature to a predetermined maximum. This may be achieved by incorporating ferromagnetic materials with a Curie temperature, a compensation temperature, a martensitic transformation or some other suitable magnetic transformation at the required temperature, called $T_c$, into the microcapsules. The requirement would be that a suitably large MHE is available for T<Tc and MHE≈0 for T>$T_c$.

The microcapsules may be formed of bio-degradable or non-biodegradable material. Preferably, the microcapsules used in the present invention are not degradable and are permanently lodged in the tumour vascular network. Thus, they can be used repeatedly to generate localised tumour heating. By subjecting the tumour bearing organ to a magnetic field, the ferromagnetic material contained within the microcapsules will heat causing highly localised tumour heating, with preservation of the surrounding normal parenchyma.

Microcapsules may be formed by any suitable known technique (See for examples, the "Encyclopedia of Chemical Technology" KIRKO-OTTHER, Vol. 15 Wiley-Interscience). For example, ferromagnetic particles may be added to a protein solution, such as an albumin solution. The resulting protein solution should preferably then be added to an oil phase that is continually agitated thereby forming an emulsion. The proteinaceous material may then be cross-linked using heat, or chemical reagents such as glutaraldehyde to form microcapsules having ferromagnetic particles trapped therein.

In an alternative method, ferromagnetic particles may be added to a solution containing Biopol in dichloromethane. The mixture is preferably then dropped into a beaker containing poly-vinyl alcohol or the like while being mixed with a homogenising mixer. The mixture should then be left to slowly mix for a suitable period of time to allow the dichloromethane to evaporate. Microcapsules thus formed may then be washed and size fractionated to select particles of a preferred size for use in the method of the invention. Preferably, the preparation is also density fractionated to select for particles of a preferred density.

In one embodiment of the invention, microcapsules composed of a material which is non-toxic to and preferably inert to or compatible with an animal and which has incorporated there within at least a ferromagnetic material, are targeted (either directly or indirectly) to and delivered to diseased tissue in a patient. The diseased tissue containing the microcapsules is then subjected to a rotational magnetic field such that the product of f, H and r is less than 7.5×10$^7$ A/s for sufficient time to treat the tissue. The time required to treat such tissue will depend on the heat generated by the microcapsules which depends on the magnetic field used and the properties of the microcapsules employed.

A variety of administration routes are available for use in the treatment of a human or animal patient. The particular mode of administration selected will depend, of course, upon the particular condition being treated and the number of microcapsules required for therapeutic efficacy. The method of this invention, generally speaking, may be practised using any mode of administration that is medically acceptable, which is capable of selectively delivering microcapsules to diseased tissue without causing clinically adverse effects and which is capable of delivering microcapsules to diseased tissue in a patient, such that the microcapsules are distributed in a substantially even manner throughout the diseased tissue. Such modes of administration might include parenteral (eg. subcutaneous, intramuscular intra-arterial and intravenous) routes.

In one embodiment of the invention microcapsules are preferably delivered by injection of a microcapsule suspension into the arterial (or portal venous) blood supply of the diseased tissue. Compositions suitable for parenteral administration conveniently comprise a sterile aqueous preparation of the capsules, which is preferably isotonic with the blood of the recipient. The sterile preparation may be an injectable solution or suspension in a non-toxic parentally acceptable diluent or solvent. Among the acceptable vehicles and solvents that may be employed are water, ringer's solution and isotonic sodium chloride solution.

The number of microcapsules per unit volume of tissue that may be used in the method will depend entirely on the amount of diseased tissue that is to be treated in a patient. Preferably, the number of microcapsule per gram of tissue is in the range of 5,000 to 300,000 (microcapsules/g). Most preferably, the range if 10,000 to 100,000, with 40,000 to 70,000 being desirable. For example, n is about 60,000 microcapsules per cubic centimetre of tumour tissue.

If, for example, the invention is used to treat a tumour or cancerous tissue, the microcapsules should be embolised into the vascular network of the tumour containing tissue so that the capsules concentrate within the tumour compartment while sparing the surrounding normal parenchyma.

The vasculature of the border area between normal tissue and the infiltrating tumour consists mainly of arterioles with adrenergic receptors, whereas vessels within the tumour lose these characteristics. Although the tumour vascular bed has little blood flow regulation, the arteriolar supply to the tumour which resides in the adjacent normal tissue is subject to normal vasomotor control. This loss of blood flow regulation in tumours underscores the principal reason why tumours cannot dissipate heat at the same rate as the ambient normal tissue when subjected to conditions of increased heat input, thus resulting in preferential heating of tumour tissue.

Progressive tumour growth results in the central region of tumours becoming relatively avascular and hypoxic. These areas do usually still contain collapsed blood vessels capable of transmitting blood flow under the influence of some vasoactive agents. The ability to lodge microcapsules containing ferromagnetic material into the vascular bed of tumour tissue can be enhanced by manipulation of the blood flow of the tumour and surrounding tissues using vasoactive agents. In one embodiment of the invention the microcapsules are preferably administered to diseased tissue under the control of vasoactive drugs. Most preferably, normal parenchyma is treated with vasoconstrictive drugs to prevent microcapsules from entering that tissue.

The combined delivery of microcapsules loaded with ferromagnetic materials, and vasoactive agents such as Angiotensin II, Noradrenaline plus beta blockade, Vasopressin, Epinephrine or other vasoactive agents may open up the collapsed microcirculation in the central portions of tumours and provide access for the deliver of microcapsules into these regions. On cessation of the effect of the vasoactive agent the central portions of tumours would return to hypovascular and hypoxic state, but would be rendered susceptible to hyperthermia damage.

The phenomenon of physiological unresponsiveness of tumour blood vessels may thus be manipulated to allow microcapsules to be selectively targeted to tumour tissue. The infusion of vasoconstrictor drugs into the arterial circulation of tumour bearing organs will cause a transient vasoconstriction of the vessels supplying the normal tissue but not those supplying the tumour. When microcapsules are introduced into the arterial circulation immediately following infusion of vasoactive drugs, the microcapsules will be preferentially directed to and trapped in the tumour vascular network and not normal tissues. The effect of the vasoactive drug will wear off within several minutes. However, by then the microcapsules will be firmly lodged in the tumour capillary network. Conversely, vasodilatory drugs may be used to selectively target radioprotectant or thermoprotectant agents to the normal non-tumour tissues.

The advantages of delivering ferromagnetic microcapsules via the vascular route compared to direct injection may be summarised as:

(i) arterial delivery of microcapsules in combination with vasoactive drug treatment allows even or substantially even distribution of the microcapsules through diseased tissue without delivery of microcapsules to normal parenchyma. In contrast, injection of microcapsules directly into diseased tissue does not result in even or substantially even microcapsule distribution. In such circumstances, microcapsules when injected into diseased tissue, focus at highest concentration, around the injection site. The density of microcapsules per unit volume of diseased tissue progressively decreases when moving away from the focal point of injection.

(ii) arterial delivery of microcapsules reduces the risk that secondary tumours will be missed, as might be the case with microcapsule delivery via injection.

(iii) arterial delivery of microcapsules avoids the need for surgical access to all tumours.

(iv) arterial delivery of microcapsules avoids the likelihood of tumour cells being spread, which might occur when a tumour is punctured by a needle.

According to a further embodiment of the invention, microcapsules loaded with ferromagnetic particles are introduced into a tumour, or a tissue containing a tumour, in conjunction with one or more vasoactive agents. A rotational magnetic field is then applied to the locus of the tumour to induce heating either by hysteresis heating or eddy current heating of the ferromagnetic particles.

Any rotational magnetic field generating means capable of delivering desired field strengths and frequencies may be employed in the present invention. A rotational magnetic field is described mathematically as the superposition of two orthogonal linear alternating magnetic fields with a $\pi/2$ phase difference, i.e. (from before)

$$H = H_x \sin(2\pi ft) + H_y \sin(2\pi ft + \pi/2) \qquad (3)$$

where $H_x$ and $H_y$ are linear alternating magnetic fields which combine to give H and W is their frequency of alternation. Any device capable of producing a magnetic field that is described mathematically by equation (3) in a region of space large enough to encompass a human torso would be suitable for use in the described application.

It will be appreciated that the operating frequency and field strength employed in the rotational magnetic field generating means should be selected subject to the characteristics of the ferromagnetic material encapsulated in the microcapsules. The field strength and frequency must also satisfy the constraint that the product $f.H \leq 5 \times 10^8$ A/m.s (assuming whole body exposure) with $f \geq 10$ kHz. Preferably the rotational magnetic field generating mean's operates at a field value corresponding to the peak in W (see FIG. 1).

Preferably the rotational magnetic field generating means used in the method is capable of producing the required rotational magnetic field conditions in a region of space large enough to accommodate part or all of human patient. Moreover, the device is preferably capable of maximising the MHE of the microcapsules.

Described below are two different examples of configurations of rotational magnetic field generating means that could be used in the described method, the 4-Pole machine and the Orthogonal Coil machine. There are, however, other possibilities that may be suitable for use in the method, which possibilities will be known to those of ordinary skill in this art.

The 4-Pole Machine

Figure 2:
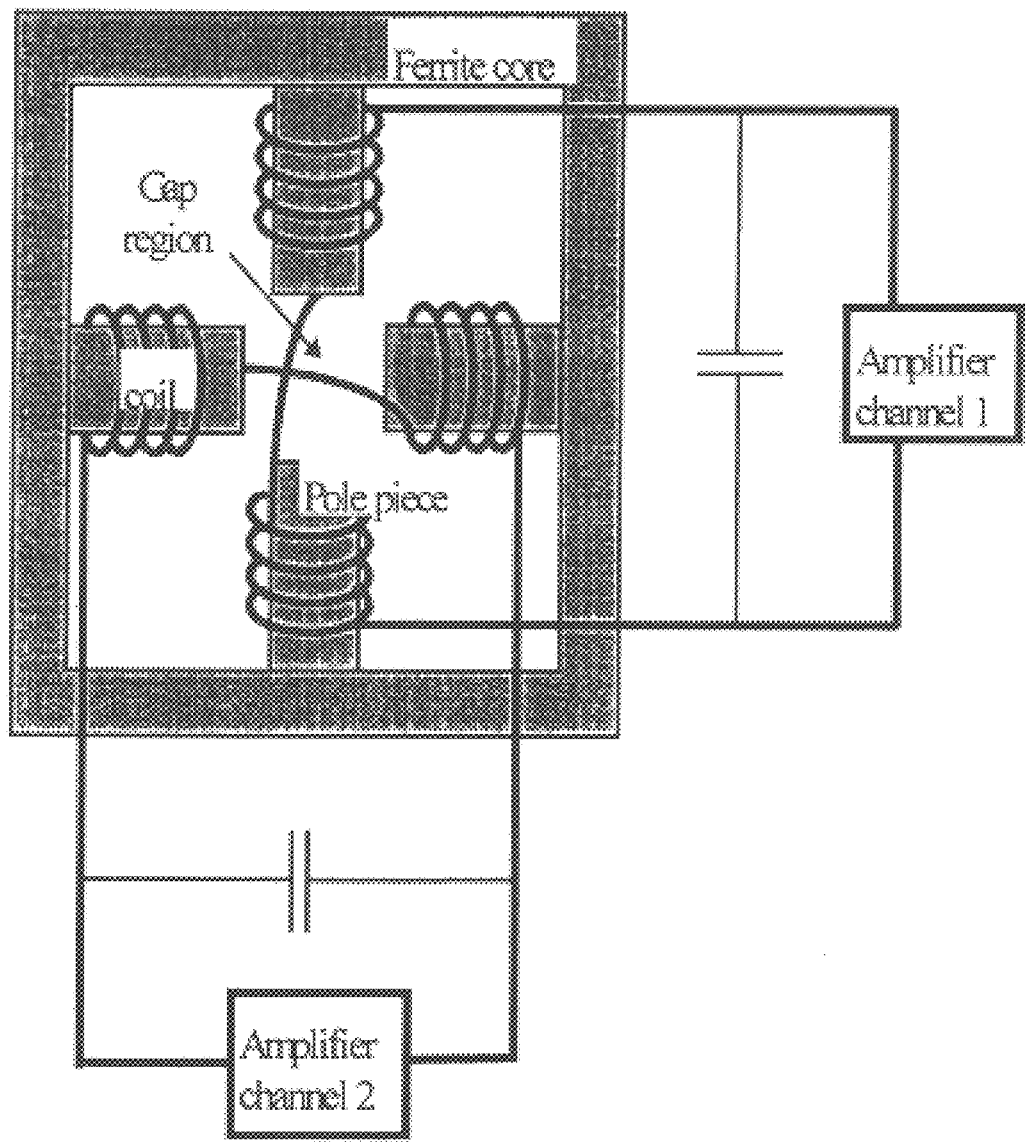
FIG. 2 shows a circuit that could be used to generate a rotational magnetic field.

The operating principles and basic design concepts of the 4-pole machine are the same as for the circuit shown in FIG. 2 used to measure the rotational hysteresis properties of ferromagnetic samples. The rotating field is produced in the gap region between the poles that must be large enough to encompass a human torso, i.e. approximately 60 cm by 60 cm.

Figure 3:
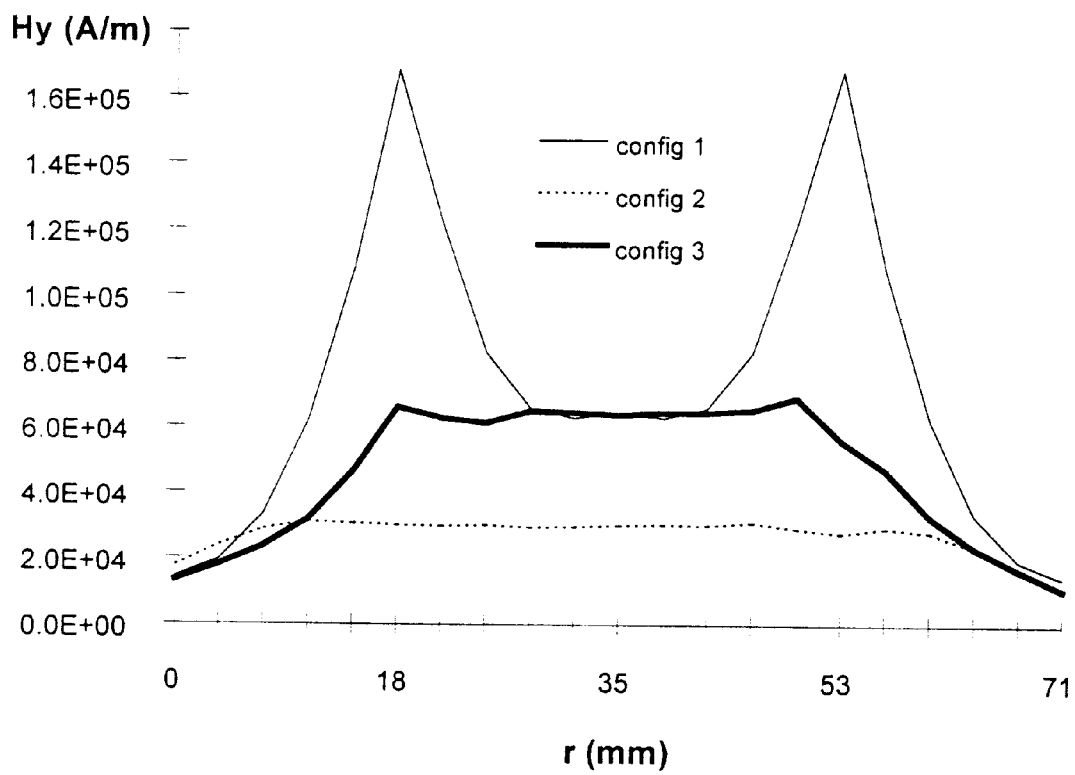
FIG. 3 illustrates calculated magnetic field uniformity for 3 different pole piece configurations.

The advantages of this configuration are that it is possible to control patient exposure to the magnetic field by judicious shaping of the pole pieces and also to minimise the power supply requirements. Modelling of the field distribution in the circuit shown in FIG. 2 was performed using a finite element modelling package (Elcut 3.0A, TOR Cooperative Enterprises) specifically for the analysis of magnetostatic problems. FIG. 3 shows the results of calculations of $H_y$ for three different pole configurations along a contour running diagonally across the gap region for the case where the magnitude of the magnetic field is maximum between the top and bottom poles ($H_y$ is maximum) and zero between the two horizontal poles ($H_x=0$). In configuration 1 the pole pieces were not tapered and were contacting at the edges, in configuration 3 the sides of each pole were tapered and for configuration 2 they were removed altogether.

When using a 4-Pole machine consideration needs to be given to the overall weight of the device and the unwanted generation of heat within the core material itself. Several different core materials can be used in such devices including ultrathin amorphous alloy laminations, a machinable metallic core material designed for high frequency use known as Fluxtrol, and sintered ferrite. Preferably, sintered ferrite material is used as the core material. To control unwanted generation of heat there may also be incorporated into the machine at least a means for cooling the core material. For example, water coding chanels could be incorporated into the structure.

Orthogonal Coil Machine

An alternative to the 4-pole machine is the orthogonal coil machine. In this machine two short, large diameter coils intersecting at right angles to each other are used to generate the rotating magnetic field (see, for example, FIG. 4). The patient is to be located inside the coils.

The advantages of this system are the relative simplicity of the design and the potentially greater access to patients. The disadvantages are that there is far less control of the field distribution leading to greater patient exposure and inferior field uniformity, increased power supply requirements compared to the 4-pole machine and increased eddy current losses in that part of each coil which is located inside the other. This last problem can be overcome for example, by using water cooled Litz wire (bundles of very thin wires) in place of solid copper tubing. The frequency and field strength will be the same as for the 4-pole device. Further reductions in operating power consumption may be possible by constructing the coils from high temperature superconducting material and cooling with liquid nitrogen. Even cooling the copper coils with liquid nitrogen will reduce power consumption from the room temperature value by 60–70%.

Unwanted heat and excessive power consumption are potential problems with the described rotational magnetic field generating means. To over come these problems the rotational magnetic field generating means are preferably produced with coils constructed from Litz wire, superconducting material and cooled in liquid nitrogen or any other material that is capable of resisting unwanted heat accumulation in the coil(s).

The shape and dimensions of the coils (in the case of the orthogonal coil machine) or the shape and dimensions of the pole pieces (in the case of the 4-pole machine) may also be refined and optimised for improved field distribution and electrical characteristics depending on the magnetic material used. For example the coils need not be perfectly cylindrical but may instead be ellipsoidal in shape.

Further features of the present invention are more fully described in the following Examples. It is to be understood, however, that the following Examples are included solely for the purposes of exemplifying the invention, and should not be understood to be in any way as a restriction on the broad description as set out above.

EXAMPLES

Example 1

Selection of Magnetic Material

This example compares the heating efficiency of a number of different magnetic materials subject to a rotational magnetic field.

Several magnetic materials were obtained from various sources (see table 1). The MHE was calculated from measurements made at different rotating magnetic field strengths using an angular acceleration magnetometer. Table 1 below lists the magnetic materials tested, the source of the material and the maximum MHE subject to the magnetic field conditions not exceeding $5 \times 10^8$ A/m.s with a frequency of at least 10 kHz.

TABLE 1

Selection of Magnetic Materials

| Magnetic Material | Source | Maximum MHE (J.m/A.g) |
| --- | --- | --- |
| Co-$\gamma$Fe$_2$O$_3$ (S11) | Bayer Chemicals | $1.1 \times 10^{-7}$ |
| $\gamma$Fe$_2$O$_3$ | BASF | $7.4 \times 10^{-8}$ |
| Magnetite | Magnox | $3.8 \times 10^{-8}$ |
| Alnico | Crumax Magnetics | $3.2 \times 10^{-8}$ |
| Chromium Dioxide | BASF | $3.0 \times 10^{-8}$ |
| Co-Fe$_3$O$_4$/Fe$_2$O$_3$ | BASF | $1.2 \times 10^{-8}$ |
| Co-$\gamma$Fe$_2$O$_3$ (PCF35HT4) | Paragon Medical | $4.3 \times 10^{-8}$ |

(The angular acceleration magnetometer works in the following way: A small quantity (approximately 5 mg) of the magnetic material under test is placed in a sample holder on the end of a thin, non-magnetic rod and located between the pole pieces of an electromagnet. The rod with the sample holder is then spun such that the magnetic sample experiences a rotating magnetic field. The rate at which the rod decelerates is measured using an optical readout system. The measured rotational deceleration gives the rotational hysteresis energy lost per cycle. This can then be used to calculate $P_{hyst}$ and, hence, MHE in equation (1) earlier.)

Example 2

Figure 4:
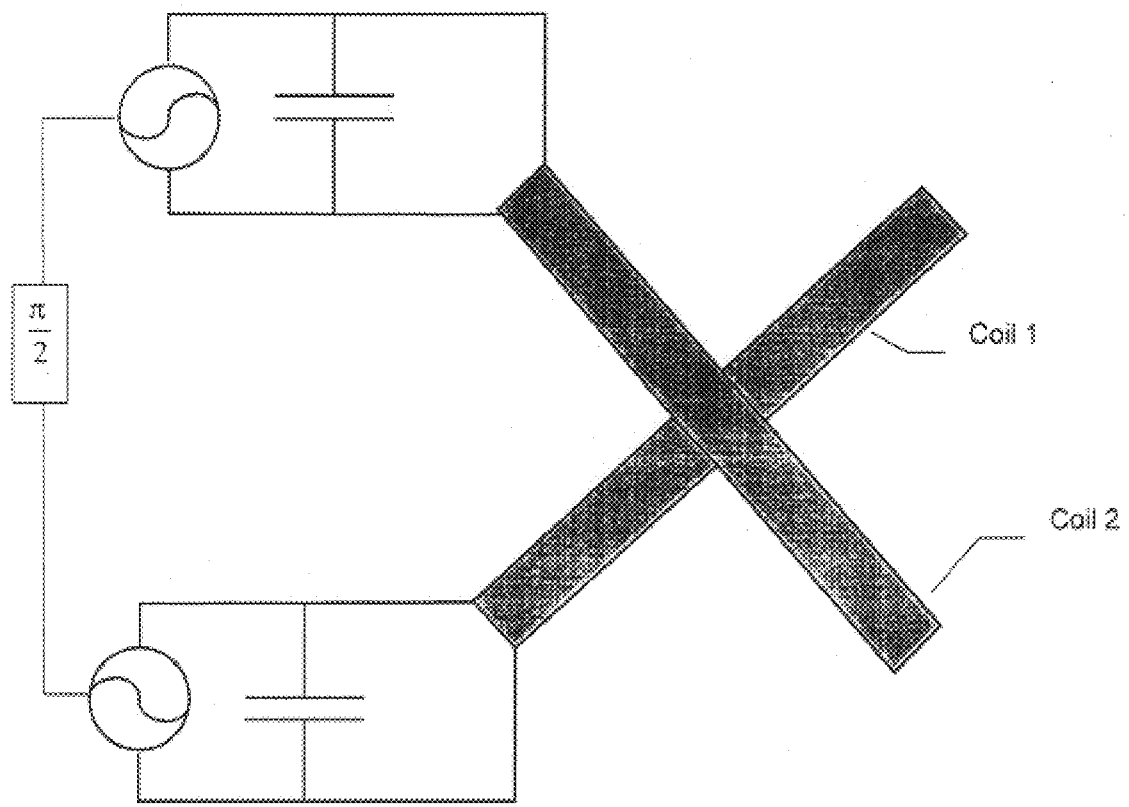
FIG. 4 is a schematic of an orthogonal coil system to generate a rotating magnetic field for measuring rotational hysteresis in magnetic samples (coils shown edge on).

Improved Heating With a Rotating Magnetic Field Compared to an Alternating Magnetic Field The circuit shown in FIG. 4 was used to compare the magnetic heating efficiency in two magnetic materials when using an applied rotating magnetic field compared to a linear alternating magnetic field. The circuit consists of two coils located at right angles to each other with a common centre point. When an alternating current is passed through either of the coils an axially directed alternating magnetic field is produced. If both coils are simultaneously energized with an alternating current at the same frequency and with a 90 degree phase difference maintained between the energizing currents then a rotating magnetic field is produced in the central region of the coils. For these tests the frequency was 21 kHz and the magnetic field amplitude was 24 kA/m.

Two test samples were made; one consisting of 20 mg of S11 magnetic material dispersed in 2 ml of agar gel and the second consisting of 20 mg of PCF35HT4 magnetic material in 1 ml of agar gel. A non-perturbing temperature probe (fluoroptic probes, Luxtron Corp) was inserted into the middle of the sample under test. The test sample was then located in the central region of the orthogonal coil pair. The sample temperature was recorded for each material firstly with only one coil energized, i.e. only a linear alternating magnetic field, and then with both coils energized to give a rotating magnetic field. The sample was allowed to cool back to the starting temperature between each test.

FIG. 5 shows the recorded temperature rise of the S11 sample for both types of magnetic field and FIG. 6 shows the same for the PCF35HT4 sample. The improved heating obtained with a rotating field compared to a linear alternating field is clearly evident.

Example 3

Comparison of Rotational vs Alternating Magnetic Heating Efficiency

Measurements of the rate of temperature rise were made for a PCF35HT4 sample at three different magnetic field strengths using the methodology described in Example 2. From this data at each field strength it is possible to calculate $P_{hyst}$ and, hence, the MHE using equation (1). As the magnetic field strength is varied the MHE is calculated subject to the magnetic field condition constraint (i.e. that the product of f and H does not exceed $5 \times 10^8$ A/m.s). The results are shown in FIG. 7 for both rotating fields and linear alternating fields. Clearly, in this example rotational fields provide superior magnetic heating efficiency.

Example 4

Site Specific Heating of Tissue

This example demonstrates that microscopic particles of magnetic material can be used to heat tissue in a site-specific manner via the mechanism of rotational hysteresis.

50 mg of the PCF35HT4 particles were firstly dispersed in 1 ml of physiological saline. A total of 20% of this mixture was injected into several sites in a freshly excised rat liver using a 2 ml syringe. All the injection sites were within 2 mm of each other. A temperature probe was inserted into the tissue at the injection site and another probe inserted into tissue approximately 15 mm away. The liver was then located into a region of rotating magnetic field produced by the circuit shown in FIG. 4. The rises in tissue temperature recorded by each of the thermometer probes while the rotating field was applied are shown in FIG. 8. The data shows that liver tissue at the injection site was heated quite significantly whilst the tissue 15 mm away did not heat at all. This is a clear demonstration that rotational hysteresis heating of small magnetic particles can effectively heat tissue in a site specific manner. Only that tissue containing the magnetic particles is heated.

Example 5

Preparation of Ferromagnetic Microcapsules 1 g of $\gamma Fe_2O_3$ particles (from Bayer Chemicals) was thoroughly mixed with a 6 ml solution containing 15% Biopol (Fluka Chemie, Switzerland) in dichloromethane. This mixture was then dropped into a beaker containing 150 ml of 0.25% polyvinyl alcohol (2.5 g of PVA 87–89% hydrolyzed, MW 124,000–186,000 dissolved in 1 Liter of water) while being mixed with a homogenising mixer set at 3900–4000 rpm. The mixture was then left mixing for 10 minutes after which it was left to mix very slowly for 60 minutes to allow all the dichloromethane to evaporate.

Microcapsules thus formed were washed successively through 63, 45 and 20 micron sieves. The fraction between 20 and 45 microns was kept. The capsules were then floated on diiodomethane, slightly diluted with acetone to give a specific gravity of 2.2. Any microcapsules that sink were disrcarded. The remainder were then washed and floated on diiodomethane diluted to a specific gravity of 1.8. The microcapsules that sink were reclaimed and washed ready for use.

It should be understood that the foregoing description of the invention including the principles, preferred embodiments and Examples cited above are illustrative of the invention and should not be regarded as being restrictive on its scope. Variations and modifications may be made to the invention by others without departing from the spirit of that which is described as the invention and it is expressly intended that all such variations and changes which fall within this ambit are embraced thereby.

We claim:

1. A method for heating a substance, comprising the steps of:
    (i) inserting at least one magnetic material having a magnetic heating efficiency of at least about $4.5 \times 10^{-8}$ J.m./A.g. when rotational magnetic field conditions are equal to or less than about $5 \times 10^8$ A/s in the substance; and
    (ii) exposing the magnetic material to a rotational magnetic field with a frequency of greater than about 10 kHz and a field strength such that the product of field strength, frequency, and the radius of the exposed region is less than about $7.5 \times 10^7$ A/s to generate hysteresis heat in the substance.

2. The method of claim 1, wherein the substance is non-biological material.

3. A method for treating biological tissue, comprising the steps of:
    (i) introducing at least one magnetic material which has a magnetic heating efficiency of at least about $4.5 \times 10^{-8}$ J.m./A.g. when rotational magnetic field conditions are equal to or less than about $5 \times 10^8$ A/s into the biological tissue; and (ii) exposing the magnetic material to a rotational magnetic field with a frequency of greater than about 10 kHz and a field strength selected such that the product of field strength, frequency, and the radius of the exposed region is less than about $7.5 \times 10^7$ A/s to generate hysteresis heat in the tissue.

4. The method of claim 3, wherein the tissue contains cancerous growths or one or more tumours.

5. The method of claim 4, wherein step (ii) is carried out for sufficient time to raise the tissue's temperature above about 42° C.

6. The method of claim 4, wherein the magnetic material is introduced into the tissue via arterial or venus blood supply.

7. The method of claim 4, wherein said exposing produces a rate of tissue heating greater than 60 mW/cm$^3$.

8. The method of claim 7, wherein the rate of tissue heating is greater than 80 mW/cm$^3$.

9. The method of claim 7, wherein the rate of tissue heating is greater than 100 mW/cm$^3$.

10. The method of claim 4, wherein the magnetic material is bound in a matrix to form microcapsules.

11. The method of claim 10, wherein the microcapsules are of a size large enough to pass through a patient's vasculature network and become dispersed and embolized within the tissue.

12. The method of claim 10, wherein the microcapsules are delivered to the tissue in conjunction with a vasoactive agent.

13. The method of claim 10, wherein the microcapsules are adapted to bind or absorb or contain a cytotoxic material which is released upon heating of the microcapsule.

14. The method of claim 10, wherein two or more different magnetic materials is introduced to the tissue, the different magnetic materials having different magnetic heating efficiency properties and bound in different matrices to form microcapsules.

15. The method of claim 14, wherein at least one of the microcapsules is adapted to release chemical, chemotherapeutic, or therapeutic substances.

16. The method of claim 10, wherein steps (i) to (ii) are repeated until the tissue or part thereof has been killed or treated sufficiently to reduce the size of the growth or tumor.

17. The method of claim 10, wherein the microcapsules are larger than about 10 microns in diameter but are smaller than about 500 microns.

18. The method of claim 10, wherein the microcapsules range in diameter from about 10 to about 100 microns.

19. The method of claim 10, wherein the microcapsules range in diameter from about 20 to about 50 microns.

20. The method of claim 10, wherein the microcapsules range in diameter from about 30 to about 40 microns.

21. The method of claim 10, wherein the microcapsules have a density which is sufficiently low to allow the microcapsules to be carried by the bloodstream in a patient.

22. The method of claim 10, wherein the microcapsules have a density in the range of 1 to 5 g/cm$^3$.

23. The method of claim 10, wherein the microcapsules have a density in the range of 1.8 to 3 g/cm$^3$.

24. The method of claim 10, wherein the microcapsules have a density in the range of 1.8 to 2.2 g/cm$^3$.

25. The method of claim 10, wherein the microcapsules have a density of about 2 g/cm$^3$.

26. The method of claim 3, wherein the magnetic material is constrained by a matrix material that does not adversely effect hysteresis or eddy current heating properties of the magnetic material.

27. The method of claim 3, wherein the magnetic material has a magnetic heating efficiency of greater than about $7 \times 10^{-8}$ J.m./A.g., when magnetic field conditions are equal to or less than about $5 \times 10^8$ A/s.

28. The method of claim 3, wherein the magnetic material has a magnetic heating efficiency of greater than about $1 \times 10^{-7}$ J.m./A.g., when magnetic field conditions are equal to or less than about $5 \times 10^8$ A/s.

29. The method of claim 3, wherein the magnetic material comprises ferromagnetic materials which include an element selected from the group consisting of iron, manganese, arsenic, antimony, and bismith.

30. The method of claim 3, wherein the magnetic material is selected from at least one of the following classes of material: $CrO_2$; gamma-ferric oxide (both cobalt treated and non-treated); metallic iron, cobalt, or nickel; ferrites of the general formula $MO.Fe_2O_3$ where M is a bivalent metal; cobalt-treated ferrites; or magnetoplumbite-type oxides (M type) with the general formula $MO.6Fe_2O_3$ where M is a large divalent ion.

31. The method of claim 3, wherein the magnetic material comprises cobalt-treated gamma-ferric oxide, a cobalt-treated ferrite, or chromium dioxide.

32. The method of claim 3, wherein the frequency is from about 10 kHz to 100 MHz.

33. The method of claim 3, wherein the frequency is from about 10 kHz to 500 kHz.

34. The method of claim 3, wherein the frequency is from about 10 kHz to 100 kHz.

35. The method of claim 3, wherein the frequency is 20 kHz.

36. The method of claim 3, wherein the magnetic material is mixed in a biocompatible liquid emulsion prior to delivery into a patient.

37. The method of claim 3, wherein an ionizing radiation is applied to the tissue in conjunction with the magnetic field.

38. The method of claim 37, wherein the radiation is applied by microcapsules which contain a radioactive compound.

39. The method of claim 3, wherein the magnetic material is bound together using a copolymer of (R)-3-hydroxybutyric acid and (R)-3-hydroxyvaleric acid.

40. The method of claim 3, wherein the microcapsules are bound together using a copolymer of (R)-3-hydroxybutyric acid and (R)-3-hydroxyvaleric acid, having a density range of 1.8–2.2 g/cm$^3$, and range in size from 20–50 microns.

41. The method of claim 3, wherein the magnetic material is delivered to the tissue by one of the administration methods selected from the group consisting of: intratumoral, peritumoral, or intravascular administrations.

42. A method for generating hysteresis heat in a tissue, comprising:

delivering to the tissue magnetic material having a magnetic heating efficiency of at least about $4.5 \times 10^{-8}$ J.m./A.g., when the rotational magnetic field conditions are about $5 \times 10^8$ A/s or less; and exposing the tissue, containing the delivered magnetic material, to a rotational magnetic field with a frequency of about 10 kHz or greater and a field strength such that the product of field strength, frequency, and the radius of the exposed tissue is less than about $7.5 \times 10^7$ A/s to generate hysteresis heat in the tissue.

43. The method of claim 42, wherein the tissue contains at least a cancerous growth or contains one or more tumor.

44. The method of claim 43, wherein said delivery and exposure are repeated until said cancerous growth or tumor is reduced in size.

45. A method for the treatment of cancerous growth or tumors, comprising:

delivering to a tissue containing a cancerous growth or tumor, a magnetic material having a magnetic heating efficiency of at least about $4.5 \times 10^{-8}$ J.m./A.g., when the rotational magnetic field conditions are about $5 \times 10^8$ A/s or less; and exposing the tissue, containing the delivered magnetic material, to a rotating magnetic field with a frequency of about 10 kHz or greater and a field strength such that the product of field strength, frequency, and the radius of the exposed tissue is less than about $7.5 \times 10^7$ A/s to generate hysteresis heat in the tissue.

46. A composition comprising:

a magnetic material having a magnetic heating efficiency of at least about $4.5 \times 10^{-8}$ J.m./A.g., when the magnetic field conditions are about $5 \times 10^8$ A/s or less; and a matrix-forming polymer;

wherein the magnetic material is encapsulated in the polymeric matrix.

47. The composition of claim 46, further comprising a cytotoxic agent.

* * * * *